US010588944B2

(12) United States Patent
Orsi et al.

(10) Patent No.: US 10,588,944 B2
(45) Date of Patent: Mar. 17, 2020

(54) METHODS AND COMPOSITIONS FOR MANAGING REPRODUCTION

(71) Applicant: Ostara Biomedical Ltd, Liverpool, Merseyside (GB)

(72) Inventors: Nicolas Michel Orsi, Liverpool (GB); Nadia Gopichandran, Liverpool (GB); David Andrew Brooke, Liverpool (GB)

(73) Assignee: Ostara Biomedical Ltd., Liverpool (GB)

( * ) Notice: Subject to any disclaimer, the term of this patent is extended or adjusted under 35 U.S.C. 154(b) by 0 days.

(21) Appl. No.: 15/285,240

(22) Filed: Oct. 4, 2016

(65) Prior Publication Data
US 2017/0095536 A1    Apr. 6, 2017

Related U.S. Application Data

(60) Provisional application No. 62/237,017, filed on Oct. 5, 2015.

(30) Foreign Application Priority Data

Oct. 5, 2015 (GB) .................................. 1517523.5

(51) Int. Cl.
A61K 38/24 (2006.01)
A61K 47/12 (2006.01)
A61K 9/00 (2006.01)
A61K 38/19 (2006.01)
A61K 38/10 (2006.01)
A61K 38/22 (2006.01)
A61K 38/26 (2006.01)
A61K 38/09 (2006.01)
A61K 38/20 (2006.01)

(52) U.S. Cl.
CPC ............ A61K 38/24 (2013.01); A61K 9/0034 (2013.01); A61K 38/09 (2013.01); A61K 38/10 (2013.01); A61K 38/19 (2013.01); A61K 38/193 (2013.01); A61K 38/195 (2013.01); A61K 38/208 (2013.01); A61K 38/22 (2013.01); A61K 38/2271 (2013.01); A61K 38/26 (2013.01); A61K 47/12 (2013.01)

(58) Field of Classification Search
None
See application file for complete search history.

(56) References Cited

U.S. PATENT DOCUMENTS

| | | | |
|---|---|---|---|
| 6,258,998 B1 | 7/2001 | Damiani | |
| 7,204,978 B1 | 4/2007 | Robertson | |
| 2005/0148023 A1 | 7/2005 | Thadhani | |
| 2005/0272636 A1 | 12/2005 | Robertson | |
| 2006/0002937 A1 | 1/2006 | Schwaeble | |
| 2006/0008532 A1 | 1/2006 | Govardhan | |
| 2006/0177459 A1 | 8/2006 | Robertson et al. | |
| 2007/0178605 A1 | 8/2007 | Mor et al. | |
| 2008/0233113 A1 | 9/2008 | Bansal | |
| 2009/0060982 A1* | 3/2009 | Ron | A61F 6/08 424/432 |
| 2010/0093557 A1 | 4/2010 | Kumble | |
| 2011/0087192 A1* | 4/2011 | Uhland | A61K 9/0036 604/514 |
| 2011/0212975 A1 | 9/2011 | Kao et al. | |
| 2012/0015879 A1* | 1/2012 | Filicori | A61K 38/24 514/9.9 |
| 2012/0115226 A1 | 5/2012 | Stachelsheid | |
| 2014/0088346 A1* | 3/2014 | Uhland | A61K 9/0004 600/35 |
| 2015/0051441 A1 | 2/2015 | Gopichandran et al. | |
| 2016/0213749 A1 | 7/2016 | Gopichandran et al. | |

FOREIGN PATENT DOCUMENTS

| | | |
|---|---|---|
| GB | 1 393 628 | 5/1975 |
| GB | 2 003 386 A | 3/1979 |
| GB | 2521709 A1 | 7/2015 |
| JP | 2009051827 A | 3/2009 |
| WO | WO 96/21427 | 7/1996 |
| WO | WO 98/39021 A1 | 9/1998 |
| WO | WO 00/25780 A1 | 5/2000 |
| WO | WO 00/68203 A1 | 11/2000 |
| WO | WO 01/19788 A2 | 3/2001 |
| WO | WO 01/64642 A2 | 9/2001 |
| WO | WO 01/64643 A2 | 9/2001 |
| WO | WO 02/00647 A1 | 1/2002 |
| WO | WO 03/007955 A2 | 1/2003 |
| WO | WO 03/064619 A2 | 8/2003 |
| WO | WO 2004/007472 A1 | 1/2004 |
| WO | WO 2004/026333 A1 | 4/2004 |
| WO | WO 2004/085385 A2 | 10/2004 |
| WO | WO 2005/017192 A3 | 2/2005 |
| WO | WO 2005/035717 A3 | 4/2005 |
| WO | WO 2005/115456 A2 | 12/2005 |
| WO | WO 2006/001463 A1 | 1/2006 |
| WO | WO 2006/017341 * | 2/2006 .............. A61K 9/70 |
| WO | WO 2007/011759 A2 | 1/2007 |
| WO | WO 2007/088996 A1 | 8/2007 |
| WO | WO 2007/088999 A1 | 8/2007 |
| WO | WO 2007/092353 A3 | 8/2007 |
| WO | WO 2007/113682 A3 | 10/2007 |
| WO | WO 2008/070902 A1 | 6/2008 |
| WO | WO 2008/073670 A2 | 6/2008 |
| WO | WO 2009/010455 A2 | 1/2009 |
| WO | WO 2009/010871 A2 | 1/2009 |

(Continued)

OTHER PUBLICATIONS

Andrews et al., European Journal of Pharmaceutics and Biopharmaceutics, 2009; 71: 505-518 (Year: 2009).*

(Continued)

Primary Examiner — Christina M Borgeest
(74) Attorney, Agent, or Firm — Stanek Lemon Crouse & Meeks, PA

(57) ABSTRACT

The present invention relates to methods, compositions and kits for controlling, managing or manipulating the non-human mammalian female reproductive cycle. The methods include oestrus induction and/or synchronisation, induction of ovulation and/or superovulation and optionally further includes a method of providing an immunopermissive uterine environment prior to insemination or implantation of embryos.

25 Claims, 2 Drawing Sheets

(56) References Cited

FOREIGN PATENT DOCUMENTS

| WO | WO 2009/026717 A1 | 3/2009 | |
|---|---|---|---|
| WO | WO 2009/051827 A1 | 3/2009 | |
| WO | WO 2009/076618 A2 | 6/2009 | |
| WO | WO 2009/125219 A3 | 10/2009 | |
| WO | WO 2009/139784 A1 | 11/2009 | |
| WO | WO 2010/048149 A1 | 4/2010 | |
| WO | WO 2010/080537 A1 | 7/2010 | |
| WO | WO 2010/126528 * | 11/2010 | ............ A61K 38/19 |
| WO | WO 2010/126528 A1 | 11/2010 | |
| WO | WO 2010/126553 A1 | 11/2010 | |
| WO | WO 2011/015037 A1 | 2/2011 | |
| WO | WO 2011/143752 A1 | 11/2011 | |
| WO | WO 2011/159297 A1 | 12/2011 | |
| WO | WO 2012/079032 A2 | 6/2012 | |
| WO | WO 2012/080729 A2 | 6/2012 | |
| WO | WO 2012/123745 A1 | 9/2012 | |
| WO | WO 2013/093878 A1 | 6/2013 | |
| WO | WO 2014/087218 A1 | 6/2014 | |
| WO | WO 2015/022509 A1 | 2/2015 | |
| WO | WO 2015/081157 A1 | 6/2015 | |

OTHER PUBLICATIONS

Han et al. "Development of Luteinizing Hormone Releasing Hormone (LHRH) Delivery Systems for Vaginal Mucosal Route" *Archives of Pharmaceutical Research* 18(5):325-331 (1995).
International Search Report and the Written Opinion of the International Searching Authority corresponding to International Application No. PCT/GB2016/053080 (14 pages) (dated Jan. 25, 2017).
Okada et al. "Vaginal Absorption of a Potent Luteinizing Hormone-Releasing Hormone Analog (Leuprolide) in Rats I: Absorption by Various Routes and Absorption Enhancement" *Journal of Pharmaceutical Sciences* 71(12):1367-1371 (1982).
Bathini et al. "2-Aminoquinazoline inhibitors of cyclin-dependent kinases", *Bioorganic & Medicinal Chemistry Letters* 15:3881-3885 (2005).
Bromfield, "Seminal fluid and reproduction: much more than previously thought," J. Assist Reprod. Genet. 31:627-636 (2014).
Caballero et al. "2D Autocorrelation, CoMFA, and CoMSIA modeling of protein tyrosine kinases' inhibition by substituted pyrido[2,3-d]pyrimidine derivatives", *Bioorganic & Medicinal Chemistry Letters* 16:810-821 (2008).
Chaouat et al, "Immunoendocrine Networks in Pregnancy and Parturition," Regional Immunology, 1994, vol. 6, pp. 295-301.
De et al., "Expression of interleukin 1, interleukin 6 and tumour necrosis factor α in mouse uterus during the peri-implantation period of pregnancy," Journal of Reproduction and Fertility, Ltd., 1993, vol. 97, Issue 1, pp. 83-89.
Feinberg et al. "Transforming Growth Factor—β Stimulates Trophoblast Oncofetal Fibronectin Synthesis in Vitro: Implications for Trophoblast Implantation in Vivo", *J. Clinical Endocrinology and Metabolism*, 78(5):1241-1248 (1994.
Fraccaroli et al., "A potential tolerogenic immune mechanism in a trophoblast cell line through the activation of chemokine-induced T cell death and regulatory T cell modulation," Human Reproduction, 24(1):166-175 (2009).
Gopichandran et al., "Multiplex determination of murine seminal fluid cytokine," Society for Reproduction and Fertility, Reproduction, 2006, vol. 131, pp. 613-621.
Gui et al., "Effects of Acupuncture on LIF and IL-12 in Rats of Implantation Failure," Am. J. Reprod. Immunol., 37:383-390 (2012).

Hansen et al., "Mastitis and Fertility in Cattle—Possible Involvement of Inflammation of Immune Activation in Embryonic Mortality," American Journal of Reproductive Immunology, 2004, vol. 51, pp. 294-301.
Kraus et al., "Peripheral Blood Cytokine Profiling During Pregnancy and Post-partum Periods," American Journal of Reproductive Immunology, 2010, vol. 64, Issue 6, pp. 411-426.
Mas et al., "Immune Regulation at the Interface During Early Steps of Murine Implantation: Involvement of Two New Cytokines of the IL-12 Family (IL-23 and IL-27) and of TWEAK," American Journal of Reproductive Immunology, 2003, vol. 59, Issue 4, pp. 323-338.
Notification of Transmittal of the International Search Report and the Written Opinion of the International Searching Authority, or the Declaration corresponding to International Application No. PCT/GB2014/052450 dated Oct. 27, 2014.
Notification of Transmittal of the International Search Report and the Written Opinion of the International Searching Authority, or the Declaration corresponding to International Application No. PCT/GB2016/050175, dated Apr. 13, 2016.
Orsi et al. "Uterine and serum cytokine arrays in the mouse during estrus," Animal Reproduction Science, 100: 301-310 (2007).
Orsi et al., "Cytokine Networks and the Regulation of Uterine Function in Pregnancy and Parturition," Journal of Neuroendocrinology, 2008, vol. 20, pp. 462-469.
Ostanin et al, "Role of Cytokines in the Regulation of Reproductive Function," Bulletin of Exp. Biology and Medicine, 143(1): 75-79 (2007).
Ota et al., "Expression of a2 Vacuolar ATPase in Spermatozoa is Associated with Semen Quality and Chemokine-Cytokine Profiles in Infertile Men," PLoS ONE, Jul. 2013, vol. 8, Issue 7, pp. 1-7.
Schjenken et al, "Seminal Fluid and Immune Adaptation for Pregnancy—Comparative Biology in Mammalian Species," Reprod. Dom. Anim., 49(3): 27-36 (2014).
Search Report corresponding to British Application No. GB1501302.2 dated Oct. 22, 2015.
Search Report under Section 17(5) corresponding to British Application No. GB1314452.2 dated Jan. 7, 2014.
Search Report under Section 17(5) corresponding to British Application No. GB1414258.2 dated Apr. 28, 2015.
Search Report under Section 17(6) corresponding to British Application No. GB1314452.2 dated May 22, 2014.
Shuya et al, "Leukemia Inhibitory Factor Enhances Endometrial Stromal Cell Decidualization in Humans and Mice," PLoS ONE, Sep. 2011, vol. 6, Issue 9, pp. 1-11.
Svensson et al., "Macrophages at the Fetal-Maternal Interface Express Markers of Alternative Activation and Are Induced by M-CSF and IL-10," The Journal of Immunology, 2011, vol. 187, pp. 3617-3682.
Third Search Report under Section 17(6) corresponding to British Application No. GB1314452.2 dated May 22, 2014.
Torchinsky et al., "TNF-α acts to prevent occurrence of malformed fetuses in diabetic mice," Diabetologia, 2004, vol. 47. pp. 132-139.
Vujisic et al., "Ovarian follicular concentration of IL-12, IL-15, IL-18 and p40 subunit of IL-12 and IS-23," Human Reproduction, 21(1): 26-50-2655 (2006).
Zenclussen et al., "Questioning the Th1/Th2 Paradigm in Reproduction: Peripheral Levels of IL-12 are Down-Regulated in Miscarriage Patients," AJRI, 48: 245-251 (2002).
Zollner et al., "LIF and TNF alpha concentrations in embryo culture media are predictive for embryo implantation in IVF," Asian Pacific Journal of Reproduction, 2012, vol. 1, No. 4, pp. 277-282.
Search Report, GB Application No. 1 616 851.0, dated Jul. 24, 2017, 5 pages.
Search Report under Section 17 corresponding to GB Patent Application No. 1417607.7 (2 pages) (dated Mar. 13, 2015).

* cited by examiner

METHODS AND COMPOSITIONS FOR MANAGING REPRODUCTION

RELATED APPLICATIONS

This application claims priority to British Application No. GB 1517523.5, filed on Oct. 5, 2015 and U.S. Provisional Application No. 62/237,017, filed on Oct. 5, 2015. The contents of each of these applications are incorporated herein by reference in their entireties.

The present invention relates to methods and compositions for controlling, managing or manipulating the reproductive cycle of theria non-human mammals. The methods include oestrus induction and/or synchronisation, induction of ovulation and/or superovulation and optionally further includes a method of providing an immunopermissive uterine environment prior to insemination or implantation of embryos. The methods provide improvements of the success rates of pregnancy and embryo implantation and increased litter sizes. The invention provides inter alia compositions, formulations and kits for the methods of the invention.

BACKGROUND

Oestrus refers to the phase when the female is sexually receptive ("in heat"). Under regulation of gonadotropic hormones, ovarian follicles mature and estrogen secretions exerts its influence. The female then exhibits sexually receptive behaviour, a situation that may be signalled by visible physiologic changes. Oestrous synchronisation is the process of targeting female mammals to come to heat and ovulate within a short time frame (usually 36 to 96 hours) so they can be inseminated at approximately the same time to save time and costs and generally stream-line the process. Synchronization of the oestrous cycle is economically advantageous and most commonly used in agricultural animals for example to decrease the costs for artificial insemination and maximise the efficiency and profitability of milk production.

Induction and/or synchronization of oestrous cycle is routinely achieved in most theria mammalian species, by supplying different combinations of hormones; luteolytic (prostaglandin $F_{2\alpha}$, $PGF_{2\alpha}$ and its analogues) and progestative (progesterone and its analogues) factors are commonly used. Secretion of $PGF_{2\alpha}$ is the event that provokes the regression of the corpus luteum in mammals, giving way to a follicular phase which culminates in oestrus behaviour and therefore, ovulation. Oestrus can be said to be the precursor of ovulation. Administration of exogenous $PGF_{2\alpha}$, or its analogues to livestock animals such as pigs, cows and sheep, induces a rapid and controlled luteolysis. If given as a single injection, some of the females will be in non-luteal phase or in the very early or very late luteal phase and will fail to respond. The use of two injections several days apart ensures that, at the second injection, all the animals will be at the correct stage of the cycle to respond by exhibiting oestrus behaviour and ovulation. On the other hand, progestative hormones are applied during several days (either by daily supply or using systems for a slow release) for mimicking the secretory activity of a corpus luteum during the luteal phase; withdrawal of the hormones would induce a follicular phase and, thus, oestrus and ovulation. To be effective, the duration of the progestative treatment generally has to surpass the active life of a possible corpus luteum in the ovary or may be combined with a luteolytic agent.

Synchronised oestrus is also used in laboratory animal breeding programmes for convenience and economic reasons, since mating will only occur if the recipient female is in oestrus. The oestrus cycle lasts 4-5 days in the mouse and rat (equivalent to a woman's average 28 day menstrual cycle), which leads to the need to rely on a large pool of potential recipient females to take part in potential matings. Typically, 75% of rat/mice recipients are not in oestrus in randomly cycling populations, leading to large numbers of females in a starting pool. The chance of females being in oestrus (sexually receptive, in the absence of synchronised oestrus) at the right time is 1:4 to 1:5 due to the length of their cycle. Thus, if 4 recipients are required, 16 to 20 females will be caged as potential mating pairs with 16 to 20 males, which translates to a 20-25% success rate. This figure can be even lower as some females will refuse to mate with their partner. It is known from the prior art that, in mice for example, that pregnant mare serum gonadotrophin (PMSG) at 5.0 iu (or some other agent with follicle stimulating properties such as human menopausal gonadotrophin, hMG) when administered intraperitoneally acts as a trigger and can induce hyperstimulation. This regime achieves the same goal in 46-52 h by overriding the females' endogenous hypothalamo-pituitary-ovarian axis. Thereafter, 5.0 iu human chorionic gonadotrophin (hCG) administered by the same route can be used as an adjunct ovulation trigger. Although the success rates with this approach are relatively high, it involves subjecting females to a regulated procedure under the Animals (Scientific Procedures) Act 1986 (i.e. one potentially causing pain, distress or lasting harm) and requires a skilled operator. However, the most common existing strategy for oestrus synchronisation in rodents is through the "Whitten effect". In mice, this is achieved by exposing the target female animals to fresh soiled male cage bedding which will emanate male pheromones, including the ones produced by male preputial glands. Over the course of three days, this results in a proportion of the exposed female mice to come into oestrus. The efficacy of this strategy varies across units, housing arrangements, strains and individual animal characteristics, and is generally accepted to generate 40-70% synchronised females for use in timed mating experiments or as recipients for embryo transfer. A problem associated with this approach is the large variation in success rates and the requirement for a large pool of females to be used to in order to generate a guaranteed discrete sufficiently large number of oestrus females available for end users.

Ovulation induction and superovulation are terms to describe the use of injectable fertility drugs (gonadotrophins) to stimulate the ovaries to produce mature oocytes. The aim of ovulation induction is to grow and ovulate an oocyte in a female which would not normally ovulate at this point in time, whilst the aim of superovulation is to produce more than one oocyte to improve fertility in non-human mammalian females. In laboratory animals, superovulation, typically but not exclusively, is for the purposes of generating multiple oocytes for in vivo/in vitro fertilisation for basic research purposes or for creating transgenic/micromanipulated embryos and is achieved using well-established approaches. These typically involve administering pregnant mare serum gonadotrophin (PMSG), human menopausal gonadotrophin (hMG) or follicle stimulating hormone (FSH; recombinant or other) intraperitoneally. 46-52 h later (in rodents), the administration of a luteinising agent (hCG, luteinising hormone (LH) or other) can be used to trigger ovulation. A typical protocol for inducing superovulation in mice comprises the intraperitoneal administration of 5 iu PMSG and 5 iu hCG circa 48 h apart. These agents are absorbed by the peritoneum and recruit multiple follicles to develop to the pre-ovulatory stage (and to ovulation if given an adequate LH-like trigger), thus overriding the physiological hypothalamo-pituitary-ovarian control. As a result, more oocytes/follicles are produced per animal, offering the benefit of reducing the number of animals required to generate a given number of synchronous follicles or oocytes post-ovulation. A disadvantage to this approach is that it involves subjecting females to a regulated procedure (i.e. one potentially causing pain, distress or lasting harm) and requires a skilled operator in order to obviate complications such as accidental intravesical injection.

There is a need for a reliable method for oestrus synchronization, with fertile ovulation and mating, in a group of animals, in a short time-frame. This would be advantageous and of benefit for improving animal management (controlling and planning the reproduction of different individuals and groups in the animal units, in the presence or absence of superovulatory effects), biotechnology (artificial insemination, combination with gonadotrophin superovulatory protocols for embryo recovery and induction of pseudopregnant fosters for embryo transfer), research (scheduling standardized and consistent experimental groups with synchronized mates for generation of synchronized pregnancies either for stage-specific studies on embryonic development or for obtaining synchronized deliveries in studies on neonates) and wellbeing (reducing the number of experimental animals and refining animal-based study experimental plans).

BRIEF SUMMARY OF THE DISCLOSURE

According to a first aspect of the invention there is provided a method of controlling reproduction in a female non-human mammal comprising:
  (i) inducing oestrus/multifollicular recruitment by inserting intra-vaginally a first vaginal delivery system comprising an erodible composition comprising at least one follicle stimulating agent and a permeation enhancer; and/or
  (ii) inducing ovulation/luteinisation by inserting intra-vaginally a second vaginal delivery system comprising an erodible composition comprising at least one follicle stimulating agent and a permeation enhancer; and/or
  (iii) Inducing an immunopermissive uterine environment prior to implantation of an embryo or prior to insemination by inserting intra-vaginally a third vaginal delivery system comprising an erodible composition comprising at least one or more of eotaxin, RANTES, IL-12 and GM-CSF and a permeation enhancer.

Preferably step (ii) is carried out between 40 to 60 hours after step (i) and more preferably between 46 to 52 hours after step (i).

In some embodiments of the invention the first and second vaginal delivery system may be in the form of a biphasic delivery device so that a single vaginal delivery device may be used with dual function. In yet further embodiments the vaginal delivery system may be a triphasic delivery system whereby a single delivery system delivers all three functional components.

Preferably step (iii) is carried out prior to, simultaneously with (co-administration) or after step (ii).

In one embodiment of the invention where the female animal is to be either artificially inseminated or mated with a male the method may comprise steps (i), (ii) and (iii). In an alternative embodiment the method of the invention will require steps (i) and (iii). In a yet further embodiment of the invention if the female is already in oestrus the method may only require steps (ii) and step (iii). Accordingly it will be appreciated that, depending on the aspect of the reproduction process that needs to be controlled, the methods of the present invention are adapted according to a user's requirements.

Preferably, the methods of the present invention are carried out on a plurality of females at the same time.

Preferably, the vaginal delivery system is inserted intra-vaginally up to the level of the cervical os and is released so as to remain in situ.

Preferably, the erodible compositions of the vaginal delivery system release their active ingredients to the vaginal mucosa whereby the active ingredients are absorbed by the vaginal mucosa.

Preferably, the vaginal delivery system is in the form of a vaginal capsule, vaginal gel, vaginal tablet, vaginal powder, vaginal solution, vaginal pessary, vaginal cup, vaginal sponge or vaginal foam or spray. Most preferably the vaginal delivery system is in the form of a vaginal pessary. Accordingly in the instance where the first and second vaginal delivery systems are combined the vaginal pessary is a single biphasic releasing pessary alternatively all three vaginal delivery systems maybe combined to provide a triphasic releasing pessary.

Preferably, the permeation enhancer is selected from the group comprising a chelator, a surfactant, bile salts, fatty acids, non-surfactants, inclusion complexes, thiolated polymers.

Suitable chelators include, but are not limited to; EDTA, citric acid, sodium salicylates and methoxy salicylates.

Suitable surfactants include, but are not limited to; sodium lauryl sulphate, polydocanol, polyoxyethylene, polyothyethylene-9-laurylether, polyothyethylene-20-ceytylether, benzalkonium chloride, 23-lauyl ether, cetylpyridinium chloride, cetyltrimethyl ammonium bromide. Suitable bile salts include, but are not limited to, sodium glycholate, sodium deoxycholate, sodium taurocholate, sodium glycodeoxycholate and phosphatyicholine. Suitable fatty acids include but are not limited to ocatnoic acid, oleic acid, capric acid, lauric acid/proplylene glycol, methyloleate, lysophosphatidlycholine and phosphatidycholine. Suitable non-surfactants include, but are not limited to, unsaturated cyclic ureas. Suitable inclusion complexes include, but are not limited to, cyclodextrins. Suitable thiolated polymer include, but are not limited to, chitosan-4-thiobutylamide, chitosan-cysteine, poly(acrylic acid)-homocysteine, polycarbophil-cysteine, polycarbophil-cysteine/gsh, chitosan-4-thioethyl amide/gsh and chitosan-4-thioglycholic acid. Other suitable agent include but are not limited to, aprotinin, azone, cyclodextrin, dextran sulphate, menthol, polysorbate 80, sulphoxides and various alkyl glycosides.

Preferably, the at least one follicle stimulating agent of the first vaginal delivery system is selected from the group comprising pregnant mare serum gonadotrophin (PMSG), human menopausal gonadotrophin (hMG), menotrophin, follicle stimulating hormone (FSH), follitrophin-alpha, follitrophin-beta, corifollitrophin-alpha, urofollitrophin, activing, betaglycan, folistatin and any of their natural or synthetic analogues recombinant or otherwise that retain follicle stimulating properties and mixtures thereof. In addition suitable candidates include glucagon-like peptide 1 (GLP-1) and extendin-4, both of which increase FSH (and LH) levels through the kisspeptin system. Yet further examples include follistatin inhibitors, peptide YY, activin A/B, inhibin inhibitors, activin receptor blockers and kisspeptin or any other agent affecting endogenous FSH profiles through the modulation of signalling in relation to activin, follistatin, GLP-1, activins A/B, inhibin, and kisspeptin.

Preferably, the concentration of the at least one follicle stimulating agent of the first vaginal delivery system is in the range of 1.0 to 10,000.0 iu and more preferably is 10 to 5,000 iu or any integer therebetween. It will be appreciated that the level of follicle stimulating agent administered is dependent on species, strain and age of recipient. For example it is envisaged that the amount of follicle stimulating agent administered to cattle will be in the range 1,000 to 10,000 iu whereas the amount administered to a rodent will be in the range to 100 iu. It will be appreciated that in order to achieve superovulation the amount of follicle stimulating agent is required to be between 2 to 20 times the natural level in the particular species.

Preferably, the at least one luteinising agent of the second vaginal delivery system is selected from the group comprising human chorionic gonanotrophin (hCG) and its forms, total hCG, C-terminal peptide total hCG, intact hCG, free β-subunit hCG, β-core fragment hCG, hyperglycosylated hCG, nicked hCG, alpha hCG, pituitary hCG, luteinising hormone (LH), lutrophin α and any of their natural or synthetic analogues recombinant or otherwise that stimulate or promote oocyte release from the ovaries and mixtures thereof.

Preferably, the concentration of the at least one luteinising agent of the second vaginal delivery system is in the range of 1.0 to 10,000.0 iu and more preferably is 10 to 5,000 iu or any integer therebetween. It will be appreciated that the level of luteinising agent administered is dependent on species, strain and age of recipient. For example it is envisage that the amount of luteinising agent administered to cattle will be in the range 1,000 to 10,000 iu whereas the amount administered to a rodent will be in the range 5 to 100 iu. It will be appreciated that in order to achieve superovulation the amount of follicle stimulating agent is required to be between 2 to 20 times the natural level in the particular species.

Preferably, the cytokines of the third vaginal delivery system comprises any one of eotaxin, RANTES, GM-CSF and IL-12 alone or in combination.

In some embodiments of the invention the third vaginal delivery system may comprise a combination of eotaxin, GM-CSF and 11-12 in addition to one or more further cytokines.

Preferably, the third vaginal delivery system further comprises any one, two, three, four five, six, seven or eight additional cytokines selected from the group comprising, MCP-1, MIP, IL-17, IL-9, TNF-α and TGFβ. Thus, the erodible composition of the third vaginal delivery system may be, as an illustrative example, eotaxin and RANTES in addition to IL-12, MCP-1, MIP and IL-17. It is within the scope of the invention to provide a number of specific combinations of the specified cytokines for use in inducing a uterus to be more receptive or less hostile to transferred embryo, sperm or other allografted tissue using a basic double combination of eotaxin GM-CSF and IL-12.

Preferably, the IL-12 is either IL-12 p40 or IL-12p70.

Preferably, the MIP is either MIP-1α or MIP-1β.

Preferably, the third vaginal delivery system further includes any one or more of the additional cytokines selected from the group comprising IL-1α, IL-1β, IL-1ra, IL-2ra, IL-2, IL-3, IL-4, IL-5, IL-6, IL-7, IL-8, IL10, IL-13, IL-15, IL-16, IL-18, FGF, G-CSF, IFN-α2, IFN-γ, IP-10, PDGF, VEGF, Leptin, CTACK, KC, GROα, HGF, LIF, MCP-3, M-CSF, MIF, MIG, β-NGF, SCF, SCGF-β, SDF-1α, TNF-β, TRAIL and VEGF.

It will be appreciated that the third vaginal delivery system of the present invention may therefore comprise a number of different combinations for example and without limitation, eotaxin plus 1 to 50 or any number therebetween of the specified cytokines selected from the aforementioned list.

The third vaginal delivery system of the present invention are selected from the following cytokines:
 (i) any one of eotaxin, RANTES, GM-CSF and IL-12 alone or in combination; and optionally one or more additional cytokine selected from the group comprising;
 (ii) MCP-1, MIP, IL-17, IL-9, TNF- and TGFβ, and optionally one or more further additional cytokines selected from the group comprising;
 (iii) IL-1α, IL-1β, IL-1ra, IL-2ra, IL-2, IL-3, IL-4, IL-5, IL-6, IL-7, IL-8, IL10, IL-13, IL-15, IL-16, IL-18, FGF, G-CSF, IFN-α2, IFN-γ, IP-10, PDGF, VEGF, CTACK, KC, GROα, HGF, Leptin, LIF, MCP-3, M-CSF, MIF, MIG, β-NGF, SCF, SCGF-β, SDF-1α, TNF-β, TRAIL and VEGF.

It will be appreciated that the third vaginal delivery system can comprise minimally 1 and up to 50 different cytokines or any number therebetween.

Preferably, the vaginal delivery system further includes a mucoadhesive polymer. The mucoadhesive polymer may be natural or synthetic. In the instance of the mucoadhesive polymer being a natural polymer it is selected from the group comprising, but not limited to, agarose, chitosan, gelatin, hyaluronic acid, carrageenan, pectin, sodium alginate, soluable starch, karaya gum and a cellulose derivative. In the instance that the mucoadhesive polymer is synthetic it is selected form the group comprising, but not limited to, carbopol, polycarbophil, polyacrylic acid, polyacrylates, a copolymer of acrylic acid, polyethylene glycol, copolymer of methyl vinyl ether and methacrylic acid, poly-2-hydroxyethylmethyl acrylate, copolymer of acrylic acid and ethylhexlyacrylate, polymethacrylate, polyalkylcyanoacrylates, polyisobutylcyanoacrylate, polyisohexyl-cyanoacrylate, thiolated polymers, poly vinyl derivatives and polyhydroxyethylene.

According to second aspect of the invention there is provided an erodible composition for intra-vaginal delivery of at least one follicle stimulating agent.

Preferably, the at least one follicle stimulating agent of the composition is selected from the group comprising pregnant mare serum gonadotrophin (PMSG), human menopausal gonadotrophin (HMG), menotrophin, follicle stimulating hormone (FSH), follitrophin-alpha, follitrophin-beta, corifollitrophin-alpha, urofollitrophin, activing, betaglycan, folistatin and any of their natural or synthetic analogues recombinant or otherwise that retain follicle stimulating properties and mixtures thereof. In addition suitable candidates include glucagon-like peptide 1 (GLP-1) and extendin-4, both of which increase FSH (and LH) levels through the kisspeptin system. Yet further examples include follistatin inhibitors, peptide YY, activin A/B, inhibin inhibitors, activin receptor blockers and kisspeptin or any other agent affecting endogenous FSH profiles through the modulation of signalling in relation to activin, follistatin, GLP-1, activins A/B, inhibin, and kisspeptin.

Preferably, the vaginal composition delivers the at least one follicle stimulating agent to the vaginal mucosa, for transmucosal delivery of the active ingredient.

Preferably, the compositions of the second aspect of the invention are prepared as a vaginal suppository, pessary, tablet, powder, bioadhesive tablet, capsule, microparticle, bioadhesive microparticle, microcapsule, microsphere, liposome, cream, lotion, foam, spray, film, ointment, solution, gel, or a sustained release gel, tablet or capsule, or a sustained release suppository administered to the vagina or incorporated into a vaginal device.

Preferably, the concentration of the at least one follicle stimulating agent of the first vaginal delivery system is in the range of 1.0 to 10,000.0 iu and more preferably is 10 to 10,000 iu or any integer therebetween.

Preferably for domestic animals/livestock the upper limit is preferably around 10,000 iu to ensure a transvaginal delivery of around 3,000 iu.

According to third aspect of the invention there is provided an erodible composition for intra-vaginal delivery of at least one luteinising agent.

Preferably, the at least one luteinising agent of the second vaginal delivery system is selected from the group comprising human chorionic gonanotrophin (hCG) and its forms, total hCG, C-terminal peptide total hCG, intact hCG, free β-subunit hCG, β-core fragment hCG, hyperglycosylated hCG, nicked hCG, alpha hCG, pituitary hCG, luteinising hormone (LH) and any of their natural or synthetic analogues recombinant or otherwise that stimulate or promote oocyte release from the ovaries and mixtures thereof.

Preferably, the concentration of the at least one luteinising agent of the second vaginal delivery system is in the range of 1.0 to 10,000.0 iu and more preferably is 10 to 5,000 iu or any integer therebetween.

Preferably for domestic animals/livestock the upper limit is preferably around 10,000 iu to ensure transvaginal delivery of around 3,000 iu.

According to a fourth aspect of the invention there is provided an erodible composition for intra-vaginal delivery comprising at least one follicle stimulating agent for use in inducing oestrus in a non-human mammal or synchronising oestrus in a plurality of animals.

According to a fifth aspect of the invention there is provided an erodible composition for intra-vaginal delivery comprising at least one luteinising agent for use in inducing ovulation or super-ovulation in a non-human mammal.

According to a sixth aspect of the invention there is provided a kit, the kit comprising (i) a first intra-vaginal delivery system for use in inducing or synchronising oestrus; (ii) a second intra-vaginal delivery system for inducing ovulation or super-ovulation and; (iii) a third intra-vaginal delivery system for inducing an immunopermissive environment within the uterus, optionally the kit further comprising an insertion device for inserting the intra-vaginal delivery systems.

The kit may further comprise a set of written instruction.

In another aspect of the invention the kit may comprise, where the female animal is to be either artificially inseminated or naturally mated with a male the first and second intra-vaginal delivery systems or alternatively where the female is to be the recipient of a transferred embryo the kit may comprise the first and third vaginal delivery systems or if the female is already in oestrus the kit may comprise the second and third intra-vaginal delivery systems.). Accordingly it will be appreciated that, depending on the aspect of the reproduction process that needs to be controlled, the kits of the present invention are adapted according to a user's requirements.

It will be appreciated that any feature ascribed to one aspect of the invention applies mutatis mutandis to each and every other aspect of the invention.

BRIEF DESCRIPTION OF THE DRAWINGS

Embodiments of the invention are further described hereinafter with reference to the accompanying drawings, in which.

Figure 1:
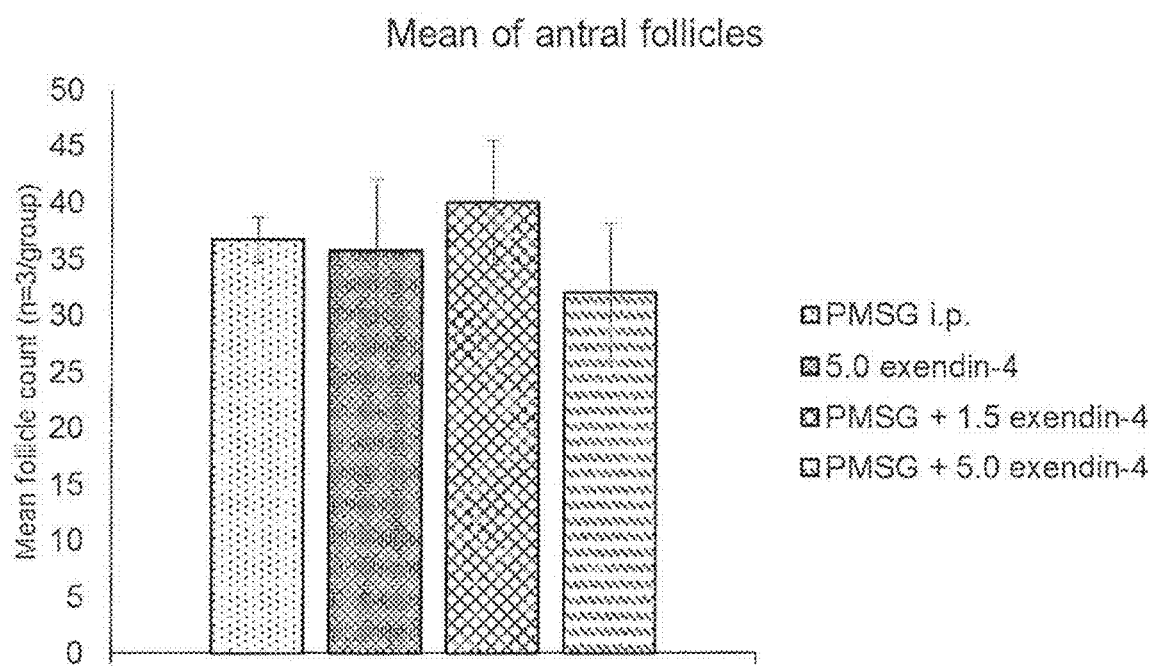
FIG. 1 shows the treatment effects on mean antral follicle counts of exemplar follicle stimulating agents by either i.p. (intraperitoneal) or p.v. (per vaginum) delivery.

Embodiments of the invention are further described hereinafter with reference to the accompanying Table, in which: Table 1 (below) shows a time chart of delivery of intra-vaginal systems with respect to matings or embryo transfer in a mouse or rat. It is also possible to perform embryo transfers up to days 4 to 5 if desired or developmental equivalents in the case of genetically modified/chimeric/cryopreserved embryos.

| PMSG PESSARY | | HCG +/− CYTOKINE PESSARY OR MATING | EMBRYO TRANSFER (RECIPIENTS)/ HARVEST (DONORS) | | | BLASTOCYST TRANSFERS (WHERE APPLICABLE) EMBRYO IMPLANTATION |
|---|---|---|---|---|---|---|
| DAY 0 | DAY 1 | DAY 2 | DAY 3 | DAY 4 | DAY 5 | DAY 6 |

Table 2 below lists the acronyms for cytokines referred to in the present invention:

TABLE 2

| Cytokines analysed using bio-plex assays | |
|---|---|
| IL-1α | Interleukin-1α |
| IL-1β | Interleukin-1β |
| IL-1ra | Interleukin-1 receptor antagonist |
| IL-2ra | Interleukin-2 receptor antagonist |
| IL-2 | Interleukin-2 |
| IL-3 | Interleukin-3 |
| IL-4 | Interleukin-4 |
| IL-5 | Interleukin-5 |
| IL-6 | Interleukin-6 |
| IL-7 | Interleukin-7 |
| IL-8 | Interleukin-8 |
| IL-9 | Interleukin-9 |

TABLE 2-continued

| Cytokines analysed using bio-plex assays | |
|---|---|
| IL-10 | Interleukin-10 |
| IL-12 (p40) | Interleukin-12 (p40) |
| IL-12 (p70) | Interleukin-12 (p70) |
| IL-13 | Interleukin-13 |
| IL-15 | Interleukin-15 |
| IL-16 | interleukin-16 |
| IL-17 | Interleukin-17 |
| IL-18 | Interleukin-18 |
| Eotaxin | Eotaxin |
| FGF | Basic fibroblast growth factor |
| G-CSF | Granulocyte-colony stimulating factor |
| GM-CSF | Granulocyte macrophage-colony stimultating factor |
| IFN-$\alpha$2 | Interferon-$\alpha$2 |
| IFN-$\gamma$ | Interferon-$\gamma$ |
| IP-10 | IFN-$\gamma$ inducible protein-10 |
| LEPTIN | Hormone associated with weight control |
| MCP-1 | Macrophage chemotactic protein-1 |
| MIP-1$\alpha$ | Macrophage inflammatory protein-1$\alpha$ |
| MIP-1$\beta$ | Macrophage inflammatory protein-1$\beta$ |
| PDGF | Platelet derived growth factor |
| RANTES | Regulated upon activation normal T cell expressed and secreted |
| TNF-$\alpha$ | Tumour necrosis factor |
| VECF | Vascular endothelial growth factor |
| CTACK | Cutaneous T cell attracting chemokine |
| KC | Ketatinocyte derived cytokine |
| GRO$\alpha$ | Growth regulated ongogene-$\alpha$ |
| HGF | Hepatocyte growth factor |
| LIF | Leukaemia inhibitory factor |
| MCP3 | Monocyte chemoattractant protein-3 |
| M-CSF | Macrophage-colony stimulating factor |
| MIF | Macrophage migration inhibitory factor |
| MIG | Monokine induced by IFN-$\gamma$ |
| $\beta$-NGF | Basic-nerve growth factor |
| SCF | Stem cell factor |
| SCGF-$\beta$ | Stem cell growth factor-$\beta$ |
| SDF-1$\alpha$ | Stromal cell derived factor-1$\alpha$ |
| TGF-$\beta$1 | Transforming growth factor $\beta$1 |
| TNF-$\beta$ | Tumour necrosis factor-$\beta$ |
| TRAIL | Tumour necrosis factor related apoptosis inducing ligand |

DETAILED DESCRIPTION

Reference herein to "controlling" reproduction is intended to include managing, manipulating or otherwise directing by external or artificial means the cycles of the reproductive processes in females. In particular embodiments, a non-human mammalian female.

Reference herein to "reproductive processes" in intended to include phases of the female reproductive cycle up to embryo implantation or implantation of fertilised oocytes by either natural mating or artificial insemination.

Reference herein to an "erodible" composition is intended to include the slow release, wearing away by natural environmental conditions, slow disintegration or diminishment of the composition so as to release the composition to the vaginal mucosa.

Reference herein to a "permeation enhancer" is intended to include any substance that facilitates permeation through the vaginal/cervical mucosa or uterine lining.

Reference herein to a "mucopolysaccharide adhesive" is intended to include any agent synthetic or natural that adheres to mucosal tissue in the vagina and that has the ability to adhere to such biological tissue for an extended period of time to improve or enhance the bioavailability of the active agent thereby enhancing permeation of the active ingredient across mucosal tissue.

Reference herein to "an agent that has follicle stimulating properties" is intended to include any natural or synthetic hormone, biologic, chemical or compound that either directly or indirectly stimulates the growth and/or recruitment of immature ovarian follicles in the ovary.

Reference herein to "a luteinising agent" is intended to include any natural or synthetic hormone, biologic, chemical or compound that is responsible for, involved in or promotes triggering the release of a mature oocyte from the ovary and/or in the establishment of a functional corpus luteum.

Reference herein to "inducing oestrus" also encompasses multifollicular recruitment.

Reference herein to "inducing ovulation" is synonymous with inducing luteinisation.

The process of mucoadhesion involving a polymeric drug delivery platform is a complex one that includes wetting, adsorption and interpenetration of polymer chains amongst various other processes. The success and degree of mucoadhesion bonding is influenced by various polymer-based properties such as the degree of cross-linking, chain length and the presence of various functional groupings. The attractiveness of mucosal-targeted controlled drug delivery of active pharmaceutical ingredients (APIs), has led formulation scientists to engineer numerous polymeric systems for such tasks. Formulation scientists have at their disposal a range of in vitro and in vivo mucoadhesion testing setups in order to select candidate adhesive drug delivery platforms. As such, mucoadhesive systems have found wide use throughout many mucosal covered organelles for API delivery for local or systemic effect. Evolution of such mucoadhesive formulations has transgressed from first-generation charged hydrophilic polymer networks to more specific second-generation systems based on lectin, thiol and various other adhesive functional groups.

The methods and compositions of the present invention may be used for a variety of organisms including a mammalian subject (e.g., a laboratory animal such as a rat, mouse, guinea pig, rabbit, primates, etc.), a farm or commercial animal (e.g., a cow, pig, horse, goat, donkey, sheep, etc.), or a domestic animal (e.g., cat, dog, ferret, etc.). In some embodiments, the subject is a primate subject, a non-human primate subject (e.g., a chimpanzee, baboon, monkey, gorilla, etc.) or a human. The subject may be an animal, human or non-human.

The methods and compositions of the present invention involve using a different approach for the administration of agents to synchronise oestrous cyclicity in randomly cycling animals or those exhibiting the Lee-Boot effect or seasonal/photoperiodic-related anovulation and to induce superovulation in randomly cycling animals or those exhibiting the Lee-Boot effect or seasonal/photoperiodic-related anovulation. A vaginal pessary-based approach is used to deliver one or more agents with follicle stimulating properties including, but not exclusively limited to, pregnant mare serum gonadotrophin (PMSG), human menopausal gonadotrophin (hMG) and follicle stimulating hormone (FSH; recombinant or other). 46-52 h later as in the instance of laboratory animals but longer for domestic animal species or farm animals/livestock, the administration of a luteinising agent (hCG, luteinising hormone (LH) or other) can be used to trigger ovulation. These agents are absorbed by the vaginal mucosa as they would by the peritoneal lining in the pelvis and abdomen (in prior art methods) and target the ovary achieving the same end, albeit with a modification in the doses administered in order to achieve plasma levels sufficient to trigger multifollicular development (in the case of follicle-stimulating agents) and ovulation/luteinisation (in the case of luteinising agents). The dosage administered will ultimately determine whether estrus synchronisation or superovulation are achieved. The benefits of this approach are a standardised, ethically sound and minimally invasive delivery system which can be used by minimally skilled operators. The reduction in stress to the animals means that these are more likely to engage in natural behaviour post-procedure, such as coitus, and obviates the risk associated with intraperitoneal injection, viz.: bowel or bladder perforation. The oocytes from animals superovulated in this manner can then be used for a variety of applications, including in vitro fertilisation or intracytoplasmic sperm injection. If the animals are mated, the resultant embryos can be used in a broad range of applications, including transgenics, in vitro embryo culture experiments, toxicology studies, stem cell injection or line rederivation. If the animals are used for oestrus synchronisation instead, they will be suitable for a variety of applications, including timed mating with stud males or as recipients for embryo transfer (such as for transgenic, chimaeric or line rederived embryos).

Example 1

Mice were administered with a standard intra-peritoneal injection of 5 IU pregnant mare serum gonadotrophin (PMSG) to induce ovulation during oestus or dioestrus, the control being mice were injected with 1% Brij 58. Test mice were given an intravaginal pessary loaded with 15 IU PMSG, 10% citric acid the control being a pessary loaded with 10% citric acid alone. Results shows that ovulation was achieved in mice given the standard induction by the i.p route but that mice treated with pessaries loaded with PMSG did not achieve desired release of ovarian follicles. This indicated that merely loading pessaries with active ingredients in the absence of either a permeating enhancer or a mucoadhesive is insufficient to induce ovulation.

Example 2

35 μl of a self-nanoemulsifying drug delivery (SNEDD) based formulation was administered into 3 mice, with observations over 24 hours. No adverse events were observed and the formulation was well tolerated. Full in vivo evaluation was then conducted with mice being divided into either i.p. (intraperitoneal) or p.v. (per vaginum) PMSG delivery. Mice were culled at 0, 2, 4, 6, 24 and 47 hours and ovaries/serum collected for analysis. Results showed that initial surface follicle counts at 24 and 48 hours were roughly equivalent between i.p. and p.v. PMSG delivery and that serum PMSG profiles, measured by ELISA at 0, 2, 4, 6, 24 and 47 hours with p.v. delivery broadly mirroring i.p. delivery with peak serum PMSG levels occurring in the first 6 hours (data not shown).

Example 3

Experiments were conducted to explore the use of exendin-4 as an exemplar of a follicle stimulating agent either alone, or in combination with PMSG, to increase follicular recruitment, and to determine whether exendin-4 could have the desired effects when delivered per vaginum (p.v.), thus avoiding the need to inject.

CD1 mice received either 1.5 or 5 nmol/kg body mass of exendin-4 in a 35 μl vaginal flush. Exendin-4 (RC762-12, Generon) was reconstituted according to the manufacturer's guidelines, and further diluted in sterile PBS with 0.5% BSA (A8806, Sigma-Aldrich). The treatment groups were as follows:

1. 5 IU PMSG i.p. (control)
2. 5 nmol/kg exendin-4 flush
3. 5 IU PMSG i.p.+1.5 nmol/kg exendin-4 flush
4. 5 IU PMSG i.p.+5 nmol/kg exendin-4 flush Treatments were given and animals were sacrificed by cervical dislocation 47 hr after treatment to coincide with the timing that hCG would be given in a typical superovulation protocol. Ovaries were excised and fixed in 10% formalin for 48 hr, before wax embedding. Ovary pairs were blocked together. Ovaries were sectioned at 5 μm from the first full-face section, then sections were obtained through the thickness of the ovary, with 100 μm between each section collected. Sections were stained using H&E and follicles at all stages were counted on a light microscope with a ×20 objective lens. Follicle numbers between groups were analysed using SPSS (version 21) by a Kruskal-Wallis test with follow-up pairwise comparisons (Mann-Whitney).

PMSG i.p. injections were used as a positive control in this study, and although not statistically significantly, animals treated with exendin-4 had increased primary, secondary and late antral follicles compared with the control group (data not shown).

Figure 2:
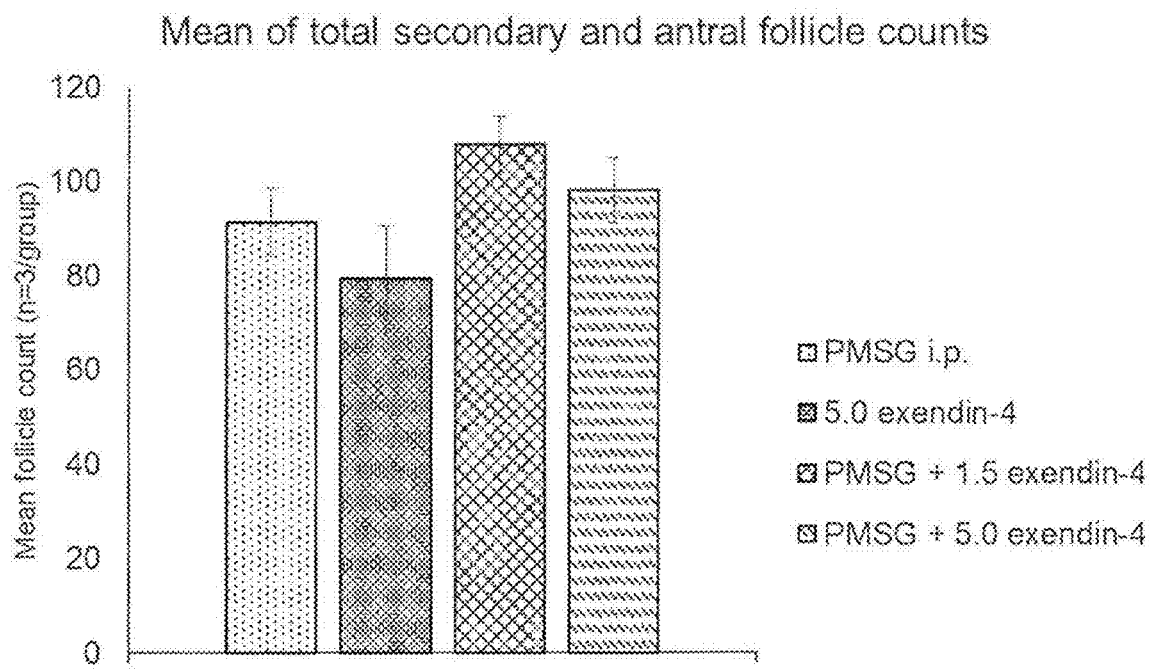
FIG. 2 shows treatment effects on mean total secondary and antral follicle counts of exemplar follicle stimulating agents by either i.p. (intraperitoneal) or p.v. (per vaginum) delivery.
Figure 3:
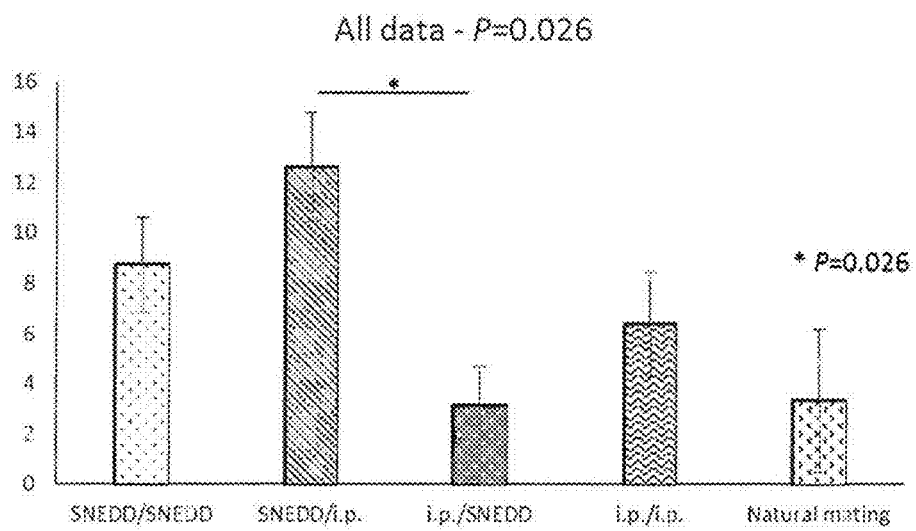
FIG. 3 shows the embryo yield using combinations of vaginally delived self-nanoemulsifying drug delivery (SNEDD) and i.p. (intraperitoneal) delivery of PMSG.

To determine the efficacy of exendin-4 in the maturation of follicles, the data were analysed on the sum of the secondary and antral follicles. FIGS. 2 and 3 show a non-significant increase in the number of the secondary and antral follicles with exendin-4 in combination with PMSG when delivered vaginally. Increasing the sample size is expected to allow this difference to reach significance.

The use of exendin-4 administered vaginally in CD1 mice resulted in an increased number of secondary plus antral follicles, which suggested that a complete superovulation protocol could yield a yet larger number of embryos.

Besides the obvious value in increasing oocyte yield for superovulation, avoiding the need to inject mice by vaginal delivery advantageously requires less training of staff, and also adheres to the 3Rs. To conclude, vaginal exendin-4 could be used as an alternative to PMSG injection to increase follicular recruitment in mice.

Example 4

Figure 4A:
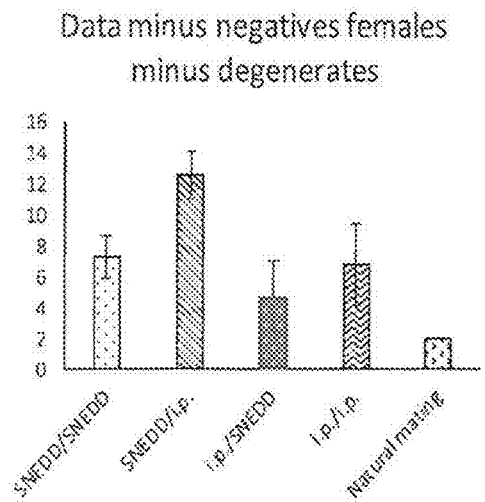
FIG. 4A shows embryo yield using combinations of vaginally delived self-nanoemulsifying drug delivery (SNEDD) and i.p. (intraperitoneal) delivery of PMSG, minus negative females and minus degenerates.
Figure 4B:
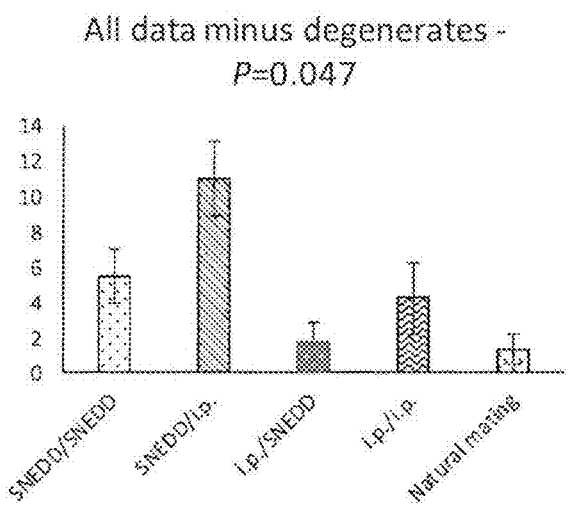
FIG. 4B shows all data minus degenerates.

Experiments were conducted to assess the efficacy of PMSG and hCG SNEDDS in the superovulation of mice by way of a double cross-over study, and to quantify embryo yield from each group after mating with an intact stud male. The dosing regimen was SNEDD (25 IU) efficacy with i.p. injection (5 IU). FIG. 3 shows, using the PMSG SNEDD followed by an i.p. hCG yielded the most embryos, which was significantly more than the i.p. PMSG/p.v. hCG group. A larger number of embryos were retrieved from the SNEDD/SNEDD (8.8) group compared with the i.p./i.p. (6.4) group, although this was not significant. FIG. 4A shows data, taking the females who did not have any embryos out of the dataset, resulted in no overall significant differences. However, removing embryos classified as degenerate showed an overall difference (FIG. 4B), but no significant difference between any of the groups.

In conclusion, there was no statistically significant difference in the cross-over study between superovulating by i.p. injection or by p.v. SNEDD treatment. The cross-over revealed that the PMSG SNEDD followed by hCG i.p. was the most successful treatment. This study confirms that vaginal delivery of biological agents involved in successful reproduction can be used as an alternative or an addition to traditional injection methods.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A method of controlling reproduction in a female mammal comprising inserting intra-vaginally an erodible composition that in situ releases multiple components in phases, the multiple components causing:
   (i) induction of oestrus/multifollicular recruitment, wherein a first component of the composition comprises at least one follicle stimulating agent and a permeation enhancer, wherein the at least one follicle stimulating agent is selected from the group consisting of pregnant mare serum gonadotrophin (PMSG), human menopausal gonadotrophin (HMG), menotrophin, follicle stimulating hormone (FSH), follitrophin-alpha, follitrophin-beta, corifollitrophin-alpha, urofollitrophin, activin, betaglycan, follistatin, glucagon-like peptide 1 (GLP-1), extendin-4, follistatin inhibitors, peptide YY, activin A/B, inhibin inhibitors, activin receptor blockers and kisspeptin;
   (ii) induction of ovulation/luteinisation, wherein a second component of the composition comprises at least one ovulation stimulating agent and a permeation enhancer, wherein the at least one ovulation stimulating agent is selected from the group consisting of human chorionic gonadotrophin (hCG), total hCG, C-terminal peptide total hCG, intact hCG, free-subunit hCG, β-core fragment hCG, hyperglycosylated hCG, nicked hCG, alpha hCG, pituitary hCG, luteinising hormone (LH); and optionally
   (iii) induction of an immunopermissive uterine environment prior to implantation of an embryo or prior to insemination, wherein an optional third component of the composition comprises at least one cytokine selected from the group consisting of eotaxin, RANTES, IL-12 and GM-CSF.

2. The method according to claim 1, wherein the erodible composition delivers the first, second and third components.

3. The method according to claim 1, wherein the method is carried out on a plurality of females at the same time.

4. The method according to claim 1, wherein the erodible composition is inserted intra-vaginally up to the level of the cervical os and is released so as to remain in situ.

5. The method according to claim 1, wherein the erodible composition releases its multiple components to the vaginal mucosa whereby the multiple components are absorbed by the vaginal mucosa.

6. The method according to claim 1, wherein the erodible composition is delivered in the form of a vaginal capsule, vaginal gel, vaginal tablet, vaginal powder, vaginal pessary, vaginal cup, vaginal sponge or vaginal foam or spray.

7. The method according to claim 1, wherein the erodible composition is in the form of a vaginal pessary.

8. The method according to claim 7, wherein the erodible composition comprises the first, second and third components.

9. The method according to claim 8, wherein the third component comprises eotaxin and RANTES or IL-12 and GM-CSF.

10. The method according to claim 1, wherein the permeation enhancer is selected from the group consisting of a chelator, a surfactant, bile salts, fatty acids, non-surfactants, inclusion complexes, thiolated polymers and combinations thereof.

11. The method according to claim 10, wherein the chelators are selected from the group consisting of EDTA, citric acid, sodium salicylates, methoxy salicylates and combinations thereof.

12. The method according to claim 10, wherein the surfactant is selected from the group consisting of sodium lauryl sulphate, polydocanol, polyoxyethylene, polyothyethylene-9-laurylether, polyothyethylene-20-ceytylether, benzalkonium chloride, 23-lauryl ether, cetylpyridinium chloride, cetyltrimethyl ammonium bromide and combinations thereof.

13. The method according to claim 10, wherein the bile salt is selected from the group consisting of sodium glycholate, sodium deoxycholate, sodium taurocholate, sodium glycodeoxycholate, phosphatylcholine and combinations thereof.

14. The method according to claim 10, wherein the fatty acid is selected from the group consisting of octanoic acid, oleic acid, capric acid, lauric acid/proplylene glycol, methyloleate, lysophosphatidlycholine, phosphatidycholine and combinations thereof.

15. The method according to claim 10, wherein the non-surfactant is an unsaturated cyclic urea.

16. The method according to claim 10, wherein the inclusion complexes comprise a cyclodextrin.

17. The method according to claim 10, wherein the thiolated polymer is selected from the group consisting of chitosan-4-thiobutylamide, chitosan-cysteine, poly(acrylic acid)-homocysteine, polycarbophil-cysteine, polycarbophil-cysteine/gsh, chitosan-4-thioethyl amide/gsh, chitosan-4-thioglycholic acid and combinations thereof.

18. The method according to claim 10, wherein the permeation enhancer is selected from the group consisting of aprotinin, azone, cyclodextrin, dextran sulphate, menthol, polysorbate 80, sulphoxides, alkyl glycosides and combinations thereof.

19. The method according to claim 1, wherein the concentration of the at least one follicle stimulating agent of the erodible composition for laboratory species of animals is in the range of 1.0 to 10,000 iu.

20. The method according to claim 1, wherein the concentration of the at least one ovulation stimulating agent of the erodible composition is in the range of 1.0 to 10,000 iu.

21. The method according to claim 1, wherein the erodible composition comprises eotaxin and RANTES or IL-12 and GM-CSF.

22. The method according to claim 21, wherein the IL-12 is IL-12 p40 or IL-12p70.

23. The method according to claim 1, wherein the erodible composition further includes a mucoadhesive polymer.

24. The method according to claim 23, wherein the mucoadhesive polymer is natural or synthetic.

25. The method according to claim 24, wherein the natural mucoadhesive polymer is selected from the group consisting of agarose, chitosan, gelatin, hyaluronic acid, carrageenan, pectin, sodium alginate, soluble starch, karaya gum, a cellulose derivative and combinations thereof and/or the synthetic mucoadhesive polymer is selected from the group consisting of carbopol, polycarbophil, polyacrylic acid, polyacrylates, a copolymer of acrylic acid, polyethylene glycol, copolymer of methyl vinyl ether and methacrylic acid, poly-2-hydroxyethylmethyl acrylate, copolymer of acrylic acid and ethylhexlyacrylate, polymethacrylate, polyalkylcyanoacrylates, polyisobutylcyanoacrylate, polyisohexyl-cyanoacrylate, thiolated polymers, poly vinyl derivatives, polyhydroxyethylene and combinations thereof.

* * * * *

UNITED STATES PATENT AND TRADEMARK OFFICE
CERTIFICATE OF CORRECTION

PATENT NO. : 10,588,944 B2
APPLICATION NO. : 15/285240
DATED : March 17, 2020
INVENTOR(S) : Nicolas Michel Orsi, Nadia Gopichandran and David Andrew Brooke It is certified that error appears in the above-identified patent and that said Letters Patent is hereby corrected as shown below:

In the Claims

Column 13, Line 54, Claim 1 change "free-subunit hCG" to -- free-β subunit hCG --.

Signed and Sealed this
Fifth Day of May, 2020

Andrei Iancu
*Director of the United States Patent and Trademark Office*